United States Patent [19]

Slavik et al.

[11] Patent Number: 4,551,134
[45] Date of Patent: Nov. 5, 1985

[54] INTRAVENOUS SET

[75] Inventors: William H. Slavik, Palos Hills; William B. Huber, Oak Park, both of Ill.

[73] Assignee: Nuvatec, Inc., Downer's Grove, Ill.

[21] Appl. No.: 406,117

[22] Filed: Aug. 6, 1982

[51] Int. Cl.$^4$ ............................................. A61M 5/16
[52] U.S. Cl. ..................................... 604/67; 604/247; 128/DIG. 13
[58] Field of Search ............... 128/DIG. 12, DIG. 13, 128/DIG. 3; 604/67, 151, 50, 65, 245, 246, 317, 247, 31; 251/139, 140, 138; 73/293, 323, 861.41

[56] References Cited

U.S. PATENT DOCUMENTS

| | | | |
|---|---|---|---|
| 3,252,623 | 5/1966 | Corbin et al. | 128/DIG. 13 |
| 3,469,574 | 9/1969 | Durkan | 604/245 |
| 3,609,379 | 9/1971 | Hildebrandt | 604/31 |
| 4,244,364 | 1/1981 | Grushkin | 128/DIG. 13 |

Primary Examiner—Lee S. Cohen
Assistant Examiner—Steven Falk
Attorney, Agent, or Firm—Willian Brinks Olds Hofer Gilson & Lione Ltd.

[57] ABSTRACT

An intravenous set is described which includes a housing which defines three separate chambers: an uppermost valve chamber, an intermediate volumetric chamber, and a lowermost drip chamber. The valve chamber is provided with an externally actuated structure for interrupting the flow of fluids into the volumetric chamber. In alternate embodiments, this valve member can include a magnetically responsive element, a diaphragm, or a pinch tube. A volumetric chamber is provided with a predetermined volume and is adapted for remote sensing of the fluid level inside the volumetric chamber. Fluids pass from the volumetric chamber into the drip chamber where they are formed into individual drops. The drip chamber is adapted to allow remote detection of drop formation and drop counting. A controller is described which, when used in conjunction with the described intravenous set, provides extremely accurately controlled rates of infusion.

23 Claims, 18 Drawing Figures

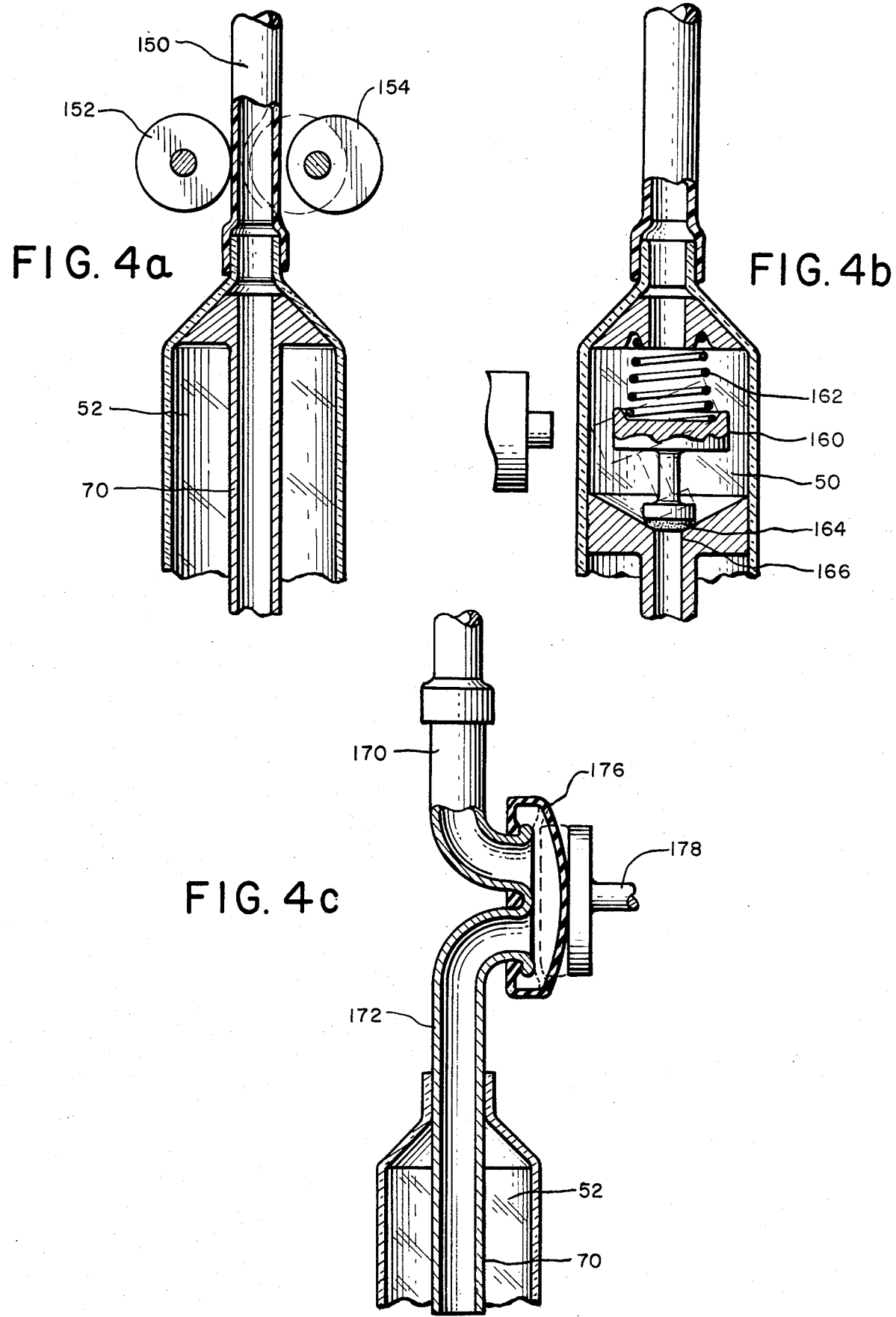

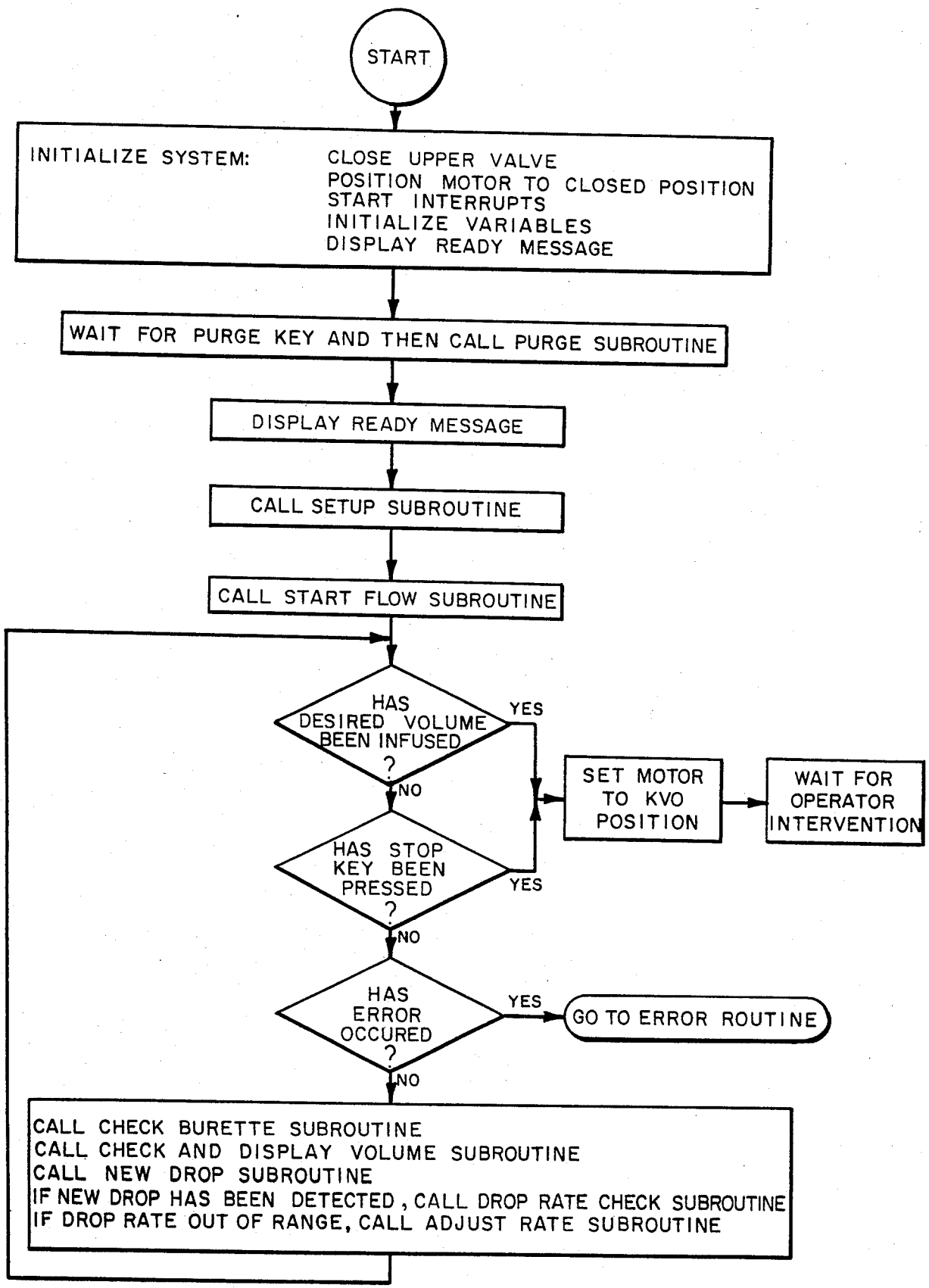

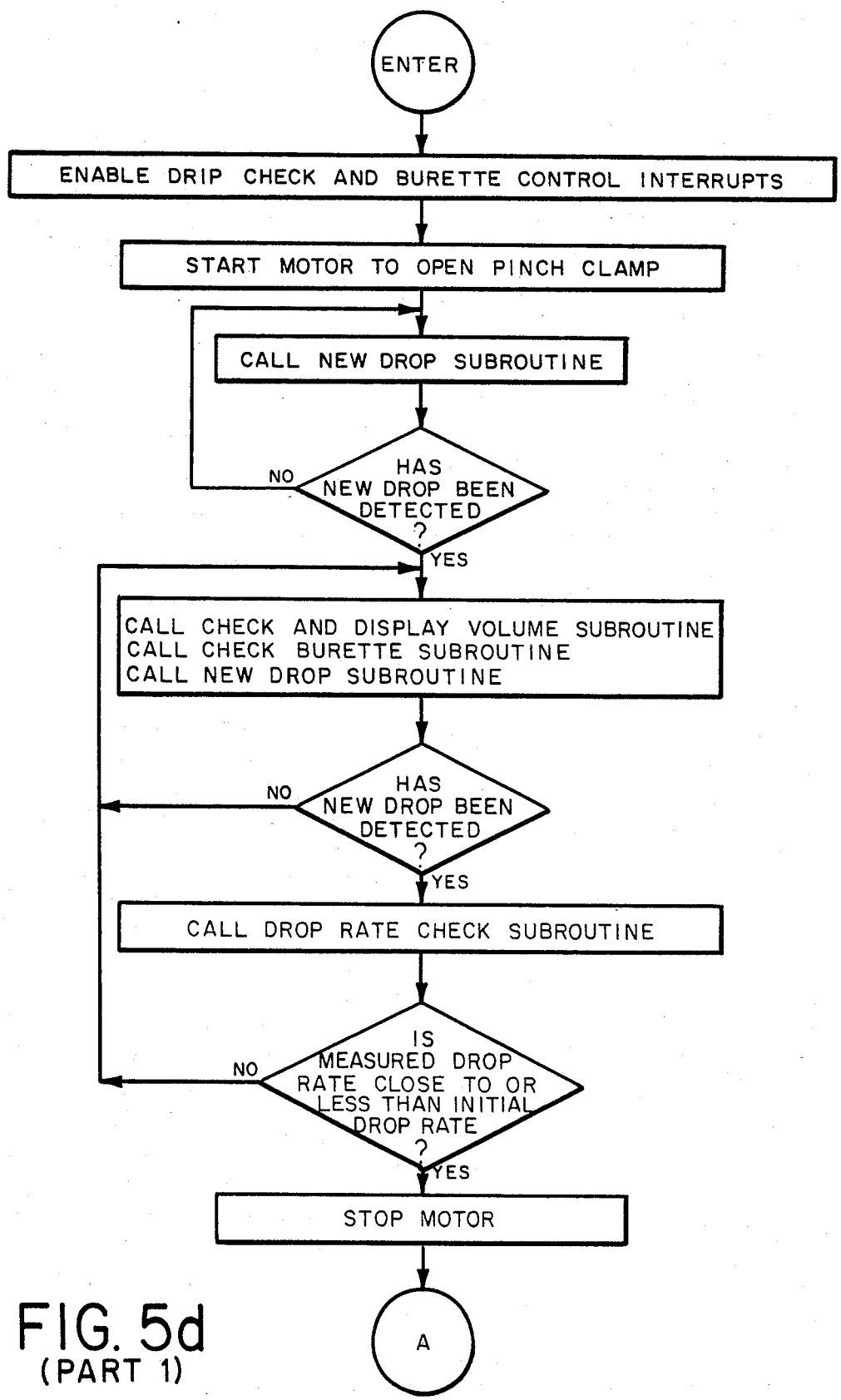
FIG. 5d (PART 1)

START FLOW SUBROUTINE (CONTINUED)

(PART 2)

INTRAVENOUS SET

BACKGROUND OF THE INVENTION

This invention relates to intravenous sets for use with flow control devices which control the rate at which fluids are passed from a container to a living subject.

A wide range of medications and nutrients are commonly administered intravenously. This is done by passing fluids containing the medication or the nutrient at a controlled rate via a needle or a cannula into a vein of a patient. Depending on the medication or nutrient being administered and the state of health of the patient, the flow rate of which fluids are infused may be critical. Furthermore, the total volume of fluid infused is typically also of interest.

In the past, two major approaches have been used to control the rate at which fluids are administered intravenously. The first approach is to use a conventional drip chamber which is manually controlled to adjust the drop rate through the drip chamber until the drops fall at a predetermined rate. This approach brings with it the advantage of simplicity in that only gravitational forces are needed to maintain the flow of fluids through the drip chamber.

However, manually controlled drip chambers are not satisfactory for all applications, for such drip chambers can permit fluid flow rate inaccuracies of as much as 30% above the requested flow rate or 60% below the requested flow rate. These inaccuracies are due to the fact that the size of individual drops passing through the drip chamber can vary as a function of the viscosity of the fluid being administered, the flow rate with which the fluid passes through the drip chamber, fluid pressure, and vibrational influences on the drip chamber. Furthermore, unless the drip chamber is carefully made to exacting tolerances, the drop volume may vary from one drip chamber to the next. This means that a drop rate appropriate for a preselected fluid flow rate with a first drip chamber is not necessarily appropriate for a second drip chamber, even if fluid viscosity and pressure are identical. Moreover, because of cold flow of tubing used in conjunction with conventional pinch clamps, a conventional, manually controlled drip chamber which is operating at a desired drop rate initially may well vary from this drop rate in time.

In an effort to provide greater accuracy of infusion rates, positive displacement infusion pumps have come into widespread use. Such pumps provide the advantage of accurately controlled infusion rates, largely independently of the pressure or the viscosity of the fluid being infused. However, such infusion pumps suffer from their own disadvantages. Because they typically operate at pressures of up to 60 psi, the danger of overpressure infusion is always present. Furthermore, infusion pumps tend to be relatively expensive, as well as heavy and cumbersome. In large part, the weight of infusion pumps is related to the size of the back up battery needed to power the pump in the event of a power failure. Because pumps operate motors on a regular basis, back up batteries for infusion pumps require large capacity. Furthermore, many infusion pumps bring with them problems related to the need to thread the IV set properly through the pump, and many infusion pumps require relatively expensive IV sets. Of course, when expensive IV sets are required for infusion pumps, it is less feasible to use the same intravenous set whether or not a pump is being used. This means that many hospitals are required to maintain stocks of two or more intravenous sets, and that a patient may well be subjected to the inconvenience of having an intravenous set replaced if the patient's physician determines that an infusion pump should be used.

SUMMARY OF THE INVENTION

The present invention is directed to an improved intravenous set which can be used to overcome the disadvantages described above. The intravenous set of this invention can be embodied in relatively inexpensive forms which can be used in conjunction with controllers to provide extremely accurate infusion rates, or which can be used alone as manually controlled IV sets. This allows a hospital to stock only a single intravenous set for use in both controlled and uncontrolled infusions.

According to this invention, an intravenous set is provided which includes an input port, first means for connecting the input port to a container, a tube, and second means for connecting the tube to an insertion device adapted to introduce fluids into a living subject. The intravenous set of this invention includes a drip chamber which comprises means for forming fluid into drops. This drip chamber is adapted to accommodate remote detection of the rate at which drops are formed by the forming means. In addition, a volumetric chamber is mounted upstream of the drip chamber such that fluid is passed from the volumetric chamber to the drip chamber. A portion of this volumetric chamber has a predetermined volume, and the volumetric chamber is adapted to allow remote detection of the fluid level inside the volumetric chamber at at least two separate levels of the volumetric chamber. The drip chamber is connected to the tube such that the tube receives fluid from the drip chamber. In addition, means are provided for connecting the volumetric chamber to the input port such that the volumetric chamber receives fluid from the input port. This connecting means includes externally actuated means for selectively and reversibly interrupting fluid flow from the input port to the volumetric chamber.

Thus, the intravenous set of this invention includes both a drip chamber, a volumetric chamber, and externally actuated means for selectively and reversibly interrupting the flow of fluid into the volumetric chamber.

As will be explained in detail below, the intravenous set of this invention can be used in conjunction with a flow controller to provide extremely accurately controlled infusion rates. When used in this way, the intravenous set of this invention provides controlled infusion rates at low cost, which can be more accurately maintained than with many infusion pumps, without the numerous disadvantages of infusion pumps suggested above. All of this is provided in an intravenous set which is relatively low in cost and which can be manufactured by standard manufacturing methods.

The invention itself, together with further objects and attendant advantages, will best be understood by reference to the following detailed description taken in conjunction with the accompanying drawings.

BRIEF DESCRIPTION OF THE DRAWINGS

FIG. 2b is a schematic view corresponding to FIG. 2a.

FIGS. 4a, 4b, and 4c are schematic views of alternate embodiments of the means for actuating the upper valve.

FIGS. 5a through 5k are flow charts of the program of the controller of FIG. 1.

DETAILED DESCRIPTION OF THE PRESENTLY PREFERRED EMBODIMENTS

Figure 1:
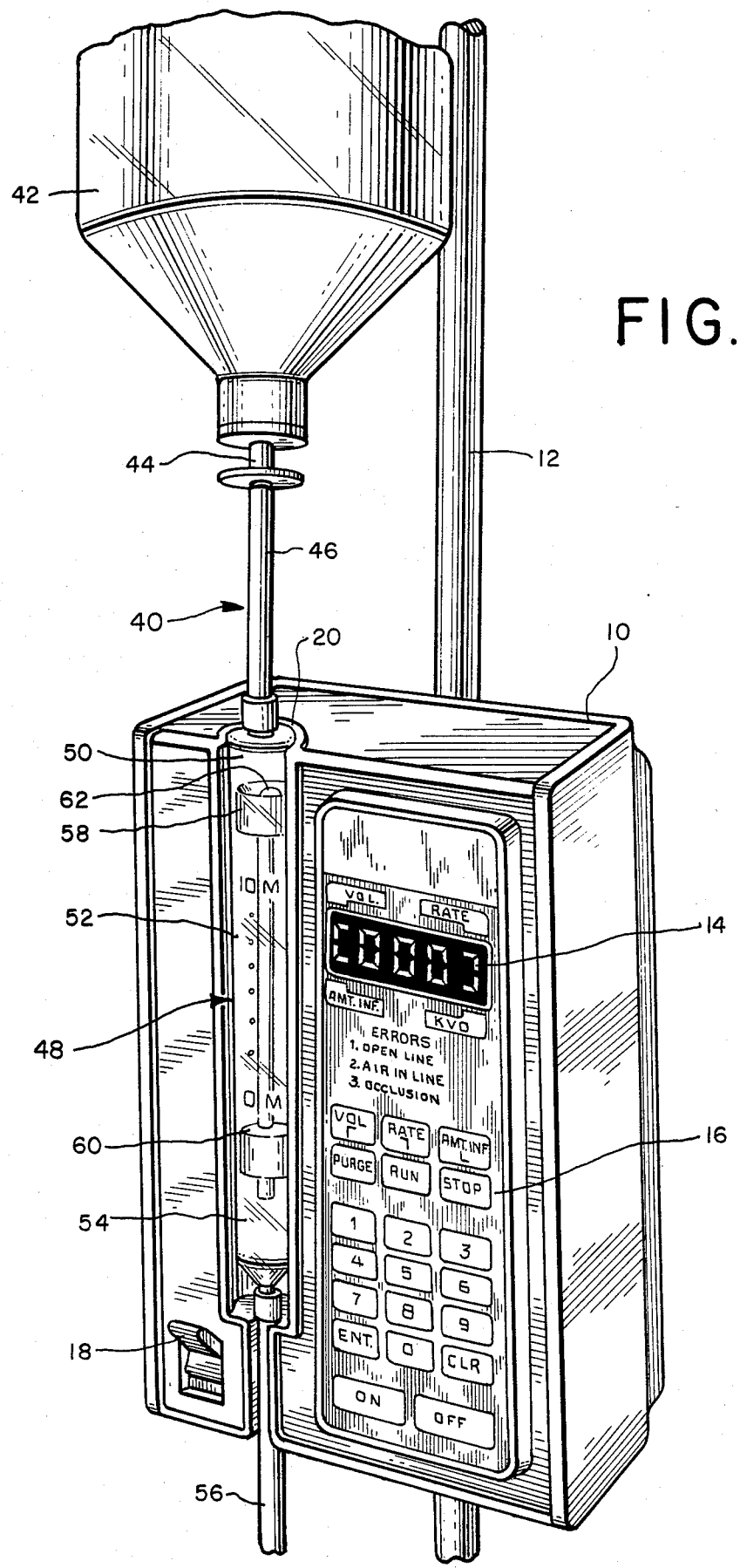
FIG. 1 is a perspective view of a presently preferred embodiment of the intravenous set of this invention installed in a flow control device.

Turning now to the drawings, FIG. 1 shows a perspective view of a presently preferred embodiment 40 of the IV set of this invention mounted in a controller 10. As shown in FIG. 1, this controller 10 is mounted on a vertically upright pole 12. The controller 10 includes a digital display 14 and a keyboard 16. The function and operation of the display 14 and the keyboard 16 will be explained below in detail in conjunction with the flow charts which form part of this specification.

The controller 10 also includes a manually operated pinch clamp lever 18 and a receiving well 20. The receiving well 20 is sized to receive and retain in place a portion of the IV set 40. As shown in FIG. 1, this IV set 40 is provided with connecting means 44 for connecting the IV set 40 to a container 42. In practice, the container 42 would contain fluids containing a nutrient or a medication to be infused intravenously into a patient.

The IV set 40 also includes an upper tube 46 which extends between the connecting means 44 and a housing 48. The housing 48 is sized to fit within the receiving well 20 such that the housing 48 can be inserted from above into the receiving well 20, but is then prevented from moving horizontally out of the receiving well 20. The housing 48 defines three separate chambers within it: an upper valve chamber 50, an intermediate volumetric chamber 52, and lower drip chamber 54. The lowermost portion of the housing 48 is coupled to a lower tube 56 which extends to means for connecting the lower tube 56 to an insertion device such as a needle or cannula adapted to introduce fluids into the patient.

The three chambers defined by the housing 48 are separated by means of an upper barrier 58 and a lower barrier 60. The three chambers 50, 52, 54 defined by the housing 48 are arranged in series such that fluid flows from the container 42 via the upper tube 46 down through the valve chamber 50, the volumetric chamber 52, and the drip chamber 54 to the lower tube 56.

Figure 2A:
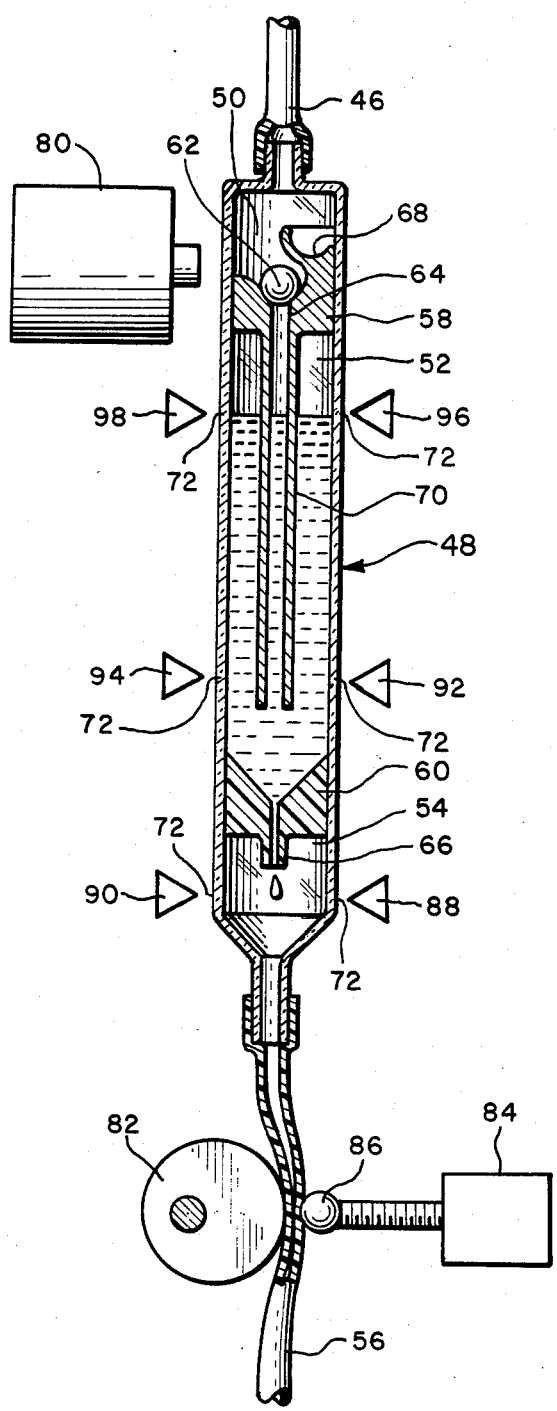
FIG. 2a is a schematic view of portions of the embodiment of FIG. 1.
Figure 2B:
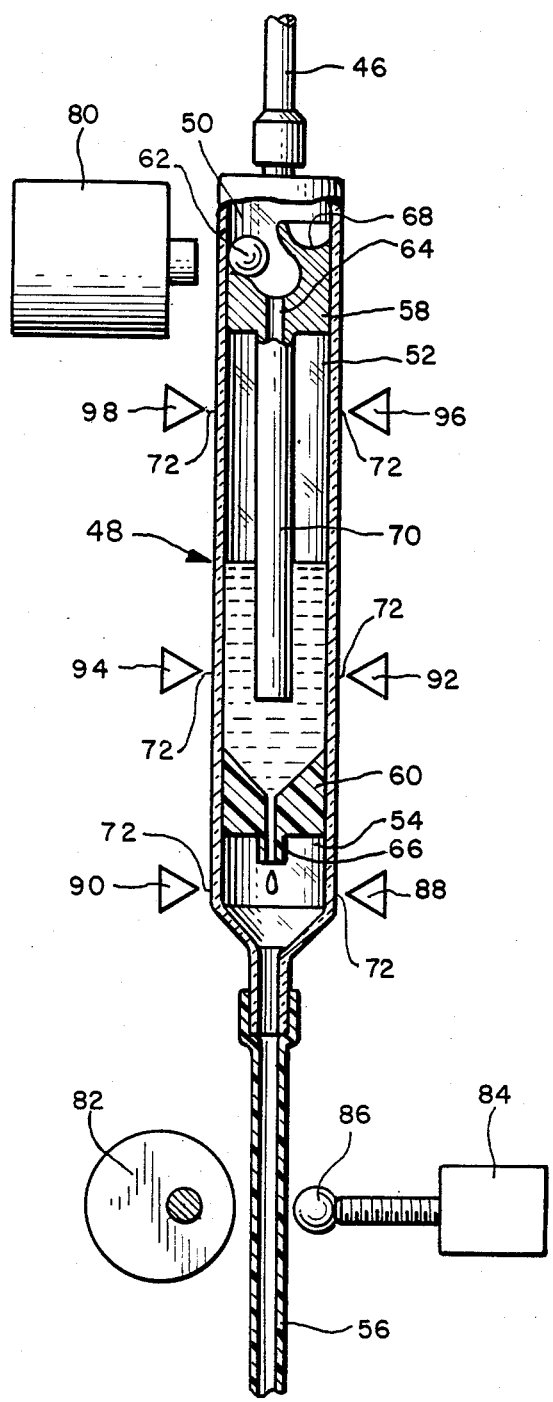

FIGS. 2a and 2b show a more schematic view of portions of the IV set 40 and the controller 10. As shown in FIGS. 2a and 2b, the upper barrier 58 of the housing 48 defines a valve seat 64 which extends between the valve chamber 50 and the volumetric chamber 52. A valve member such as a magnetically responsive ball 62 is included inside the valve chamber 50. The ball 62 is sized and adapted to position itself against the valve seat 64 in the absence of magnetic forces, and thereby to interrupt fluid flow from the valve chamber 50 into the volumetric chamber 52.

A pocket 68 is defined in an interior surface of the valve chamber 50. This pocket 68 is provided to retain the ball 62 away from the valve seat 64 when desired. By suitably manipulating the housing 48, the ball 62 can either be positioned inside the pocket 68 (in which case the valve seat 64 provides a continuously open fluid passageway between the valve chamber 50 and the volumetric chamber 52), or the ball 62 can be allowed to assume the position shown in FIG. 2a (in which case the ball 62 seals against the valve seat 64 in the absence of magnetic forces). In alternate embodiments of the IV set 40, a cap magnet cap magnet can be positioned on the exterior of the housing 48 to hold the ball 62 away from the valve seat 64 when desired.

The lower barrier 60 which separates the volumetric chamber 52 from the drip chamber 54 is provided with a drip forming device 66 at its lower end. Thus, the lower barrier 60 provides a fluid passageway which is constantly open between the volumetric chamber 52 and the drip chamber 54, and fluids passing into the drip chamber 54 are formed into individual drops by means of the drip forming device 66.

The volumetric chamber 52 is carefully sized such that the volume of the volumetric chamber 52 between two predefined levels is equal to a predetermined quantity, 10 milliliters in this example. A conduit 70 is provided which extends downwardly from the valve seat 64 to a point below the lower of these two levels. This conduit 70 serves to confine fluids entering the volumetric chamber 52 to a predetermined portion of the volumetric chamber 52 until such fluids reach a point below the lower level. As used herein, the term "volumetric chamber" is used in its broad sense to cover chambers which are defined in part by detector levels rather than physical walls. Thus, the volumetric chamber 52 is described as empty when the fluid level reaches the lower level and full when it reaches the upper level.

With respect to materials, the upper end lower tubes 46, 56 of this embodiment are formed of PVC materials. Thus, the tubes 46, 56 are flexible and collapsible. The housing 48 and the upper and lower barriers 58, 60 are formed of acetate, such that they are substantially ridid, dimensionally stable, and transparent. The transparency of the housing 48 is important in this embodiment, for the controller 10 photoelectrically senses fluid level and detects drops within the housing 48. Thus, the portions of the housing 48 adjacent the photosensors and light sources included in the controller 10 in effect act as windows 72 which pass optical signals through the housing 48. As used herein, the term "window" is used in its broad sense to include transparent and translucent regions of a housing, whether or not such regions are distinguished in any way from remaining portions of the housing.

Before proceeding to a detailed description of the manner in which the IV set 40 is used, it should be pointed out that a wide range of upper valves can be used in the IV set 40. Three alternate configurations are shown in FIGS. 4a, 4b and 4c.

As shown in FIG. 4a, one alternative approach is to eliminate the valve chamber 50 entirely from the IV set 40 and to substitue a pinch clamp in the controller 10 made up of a fixed pinch clamp jaw 152 and a motor driven pinch clamp jaw 154. These jaws 152, 154 bear against a flexible, resilient tube 150 which can for example be formed by the upper tube 46 interconnecting the housing 48 with the connecting means 44. In this alternate embodiment, it is the tube 150 which forms the means for interrupting fluid flow into the volumetric chamber 52, and this means is actuated by the jaws 152, 154.

In another alternative embodiment shown in FIG. 4b, the ball 62 is replaced with a tiltable element 160 which defines a longitudinal axis extending parallel to the length of the housing 48. This tiltable element 160 is formed of a magnetically responsive material, and it is provided with a valve portion 164 which seals against a valve seat 166. A spring 162 is provided which biases the tiltable element 160 into a sealing position, as shown in FIG. 4b. By applying magnetic forces with an electromagnet similar to the one described above in conjunction with FIGS. 1 through 3, the tiltable element 160 may be tilted to one side, thereby allowing fluid to flow downwardly through the valve seat 166 into the volumetric chamber 152. In some applications such a tilt valve may require smaller currents in the electromagnet 80 than does the ball valve of FIGS. 1, 2a, and 2b.

Yet another alternative is shown in FIG. 4c, in which an inlet tube 170 and an outlet tube 172 are coupled to a diaphragm valve 174. This diaphragm valve 174 includes a diaphragm 176. An externally situated platen 178 is provided. This platen 178 can be used to push the diaphragm 176 against the tubes 170, 172 in order to interrupt fluid flow through the diaphragm valve 174. The lower end of the outlet tube 172 is connected to pass fluid into the volumetric chamber 52.

From the foregoing discussion of FIGS. 4a, 4b and 4c, it should be apparent that a wide range of valves can be used in conjunction with the controller of this invention. In each case, the valve should be capable of remote actuation without destroying the integrity of the IV set, and without allowing foreign materials to enter the IV set.

In order fully to set out the manner in which the IV set 40 is used, the following discussion will take up in detail the structure and operation of the controller 10. As shown in FIG. 2a, the controller 10 includes an electromagnet 80 which is positioned adjacent the valve chamber 50. When the electromagnet 80 is energized the ball 62 is moved from the position shown in FIG. 2a to that shown in FIG. 2b, thereby allowing fluids to pass from the valve chamber 50 to the volumetric chamber 52.

The controller 10 also includes a user positioned pinch clamp jaw 82, the position of which is controlled by means of the pinch clamp lever 18. The jaw 82 is movable between an open position in which the lower tube 56 can freely be inserted in the controller 10, and a closed position in which the controller 10 is capable of controlling fluid flow through the lower tube 56. In the drawings, FIG. 2a schematically shows the closed position of the jaw 82 and FIG. 2b schematically shows the open position of the jaw 82. A motor 84 is provided which serves to control the position of a pinch clamp jaw 86. This jaw 86 is positioned to oppose the jaw 82, such that when the jaw 82 is in the closed position shown in FIG. 2a, the flow rate through the lower tube 56 can be controlled by means of the motor 84 and the jaw 86.

As shown in FIGS. 2a and 2b, three light sources 88, 92, 96, are positioned adjacent the housing 48 at three preselected levels. Similarly, three photosensors 90, 94, 98 are positioned in the controller 10 such that each is aligned with a respective one of the light sources 88, 92, 96. The light source 88 and the photosensor 90 cooperate to form a drop detector; the signal generated by the photosensor 90 serves as an indication of the passage of drops formed by the drop forming device 66. The light source 92 and the photosensor 94 cooperate to form a lower level fluid detector. The signal generated by the photosensor 94 varies as a function of whether the fluid level within the volumetric chamber 52 is above or below the lower level defined by the level of the photosensor 94. Similarly, the light source 96 and the photosensor 98 cooperate to form an upper level fluid detector which detects whether the fluid level in the volumetric chamber 52 is above or below the upper level defined by the photosensor 98. The conduit 70 extends within the volumetric chamber 52 to a point below the lower level light source and photosensor 92, 94. In this way, fluid entering the volumetric chamber 52 is confined to a portion of the volumetric chamber 52 which is separated from the portion of the volumetric chamber 52 viewed by the upper and lower photosensors 94, 98. Erroneous signals related to the downward flow of fluid into the volumetric chamber 52 are thereby avoided.

Figure 3:
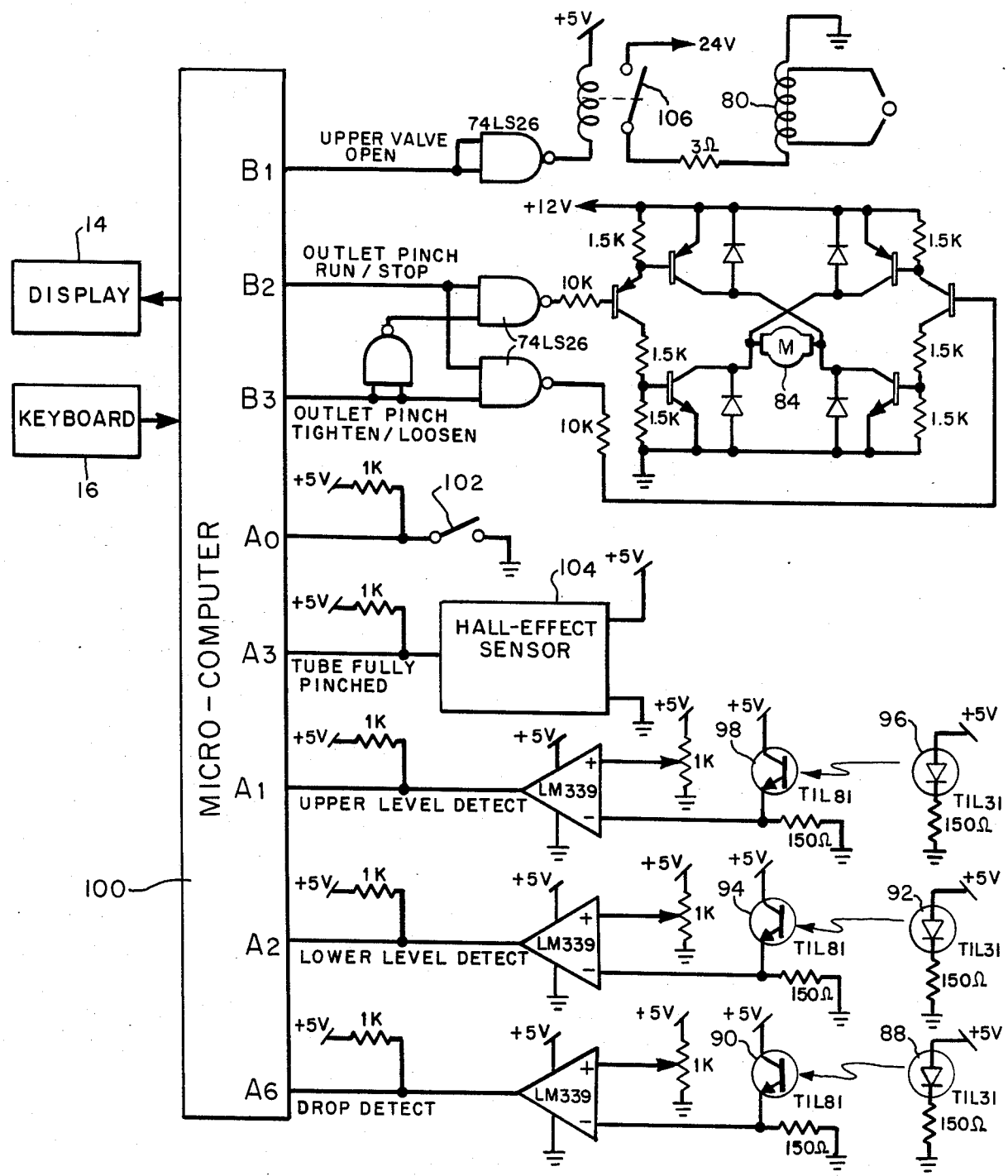
FIG. 3 is an electrical schematic diagram of the controller of FIG. 1.

FIG. 3 shows an electrical schematic of the controller 10. As shown in FIG. 3, the controller 10 includes a microcomputer 100 which is coupled to the display 14 and the keyboard 16. The microcomputer receives inputs from the three photosensors 90, 94, 98. In addition, the microcomputer 100 receives an input signal from a Hall effect sensor 104. This sensor 104 is positioned to respond to the magnetic field of a magnet (not shown) which is mounted on the motor positioned pinch clamp jaw 86. When the jaw 86 is positioned to the fully clamped position, the sensor 104 generates a signal which is applied to the computer 100 as an indication that the jaw 86 has reached the fully pinched position. A fifth input signal to the computer 100 is provided which allows the computer 100 to determine the position of the user positioned pinch clamp jaw 82. This input signal is provided by a switch 102 which changes state depending on whether the user position pinch clamp jaw 82 is positioned in the open position shown in FIG. 2b or the closed position shown in FIG. 2a.

The computer 100 is also provided with three digital outputs. The first output controls a relay 106 which in turn controls the flow of current through the electromagnet 80. In this prefered embodiment, the electromagnet 80 is formed of 2500 turns of number 26 wire on a $\frac{3}{8}$ inch bobbin having a core. Thus, the first output allows the controller 10 to open or to close the valve included in the valve chamber 50 as desired.

The second and third computer outputs are used to control the operation of the motor 84. One of these two outputs determines whether the motor 84 is running or stopped, and the other output determines the direction of the motor (i.e. whether the motor is tightening the motor positioned pinch clamp jaw 86 against the lower tube 56 or loosening the jaw 86).

Turning now to the flow charts of FIGS. 5a through 5k, the program of the microcomputer 100 will be described. An assembly language listing of this program is included in a copending application (Attorney Docket No. 7807) which names the same inventors and is assigned to the assignee of this invention.

FIG. 5a shows the Main control Sequence for the program of the computer 100. When power is applied to the computer 100, the computer 100 first initializes the controller 10. This is done by de-energizing the electromagnet 80, positioning the motor 84 to the fully pinched position, starting the program interrupts, initializing program variables, and displaying a ready message on the display 14. The program then waits for the operator to depress the Purge key included in the keyboard 16.

Figure 5B:
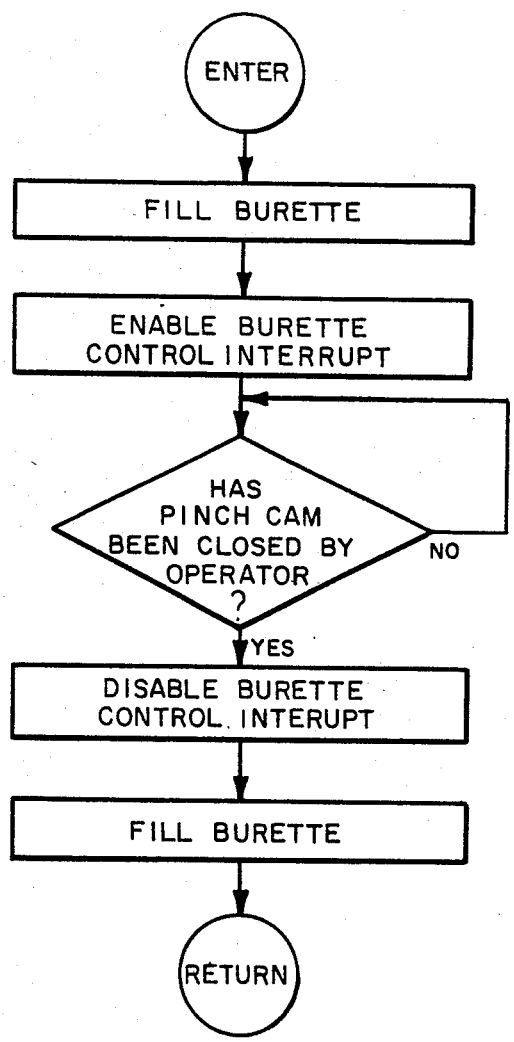

Once the Purge key is pressed, the Purge Subroutine shown in FIG. 5b is executed. This subroutine operates to fill the volumetric chamber 52 to the level of the upper photosensor 90 and to enable the burette control interrupt. In the following discussion, the term "burette" will on occasion be used to refer to the volumetric chamber 52. When the burette control interrupt is enabled, the interrupt service routine shown in FIG. 5k operates to fill the burette automatically when the burette is empty and to deenergize the electromagnet 80 when the burette is full. At this point, the controller 10 does not control fluid flow through the drip chamber 52. Rather, the controller 10 allows the user to cause an indefinite amount of fluid to be passed through the drip chamber 52. This mode of operation is provided to allow the user to purge the IV set 40 by passing fluids through the IV set 40 to remove air from the system.

Once the user is satisfied that the IV set 40 has been properly purged, the user closes the pinch clamp lever 18. The Purge Subroutine of FIG. 5b responds to the closing of the pinch clamp lever 18 by disabling the burette control interrupt and then filling the burette to the upper level.

Figure 5C:
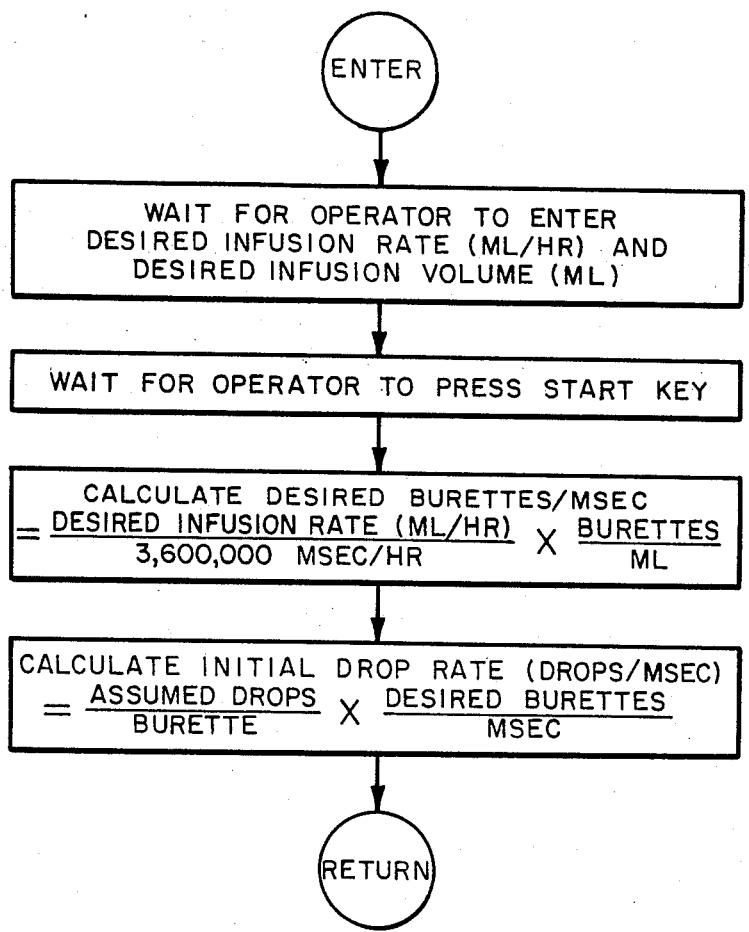

At this point, the program of FIG. 5a displays a ready message and then calls the Set Up Subroutine shown in FIG. 5c. This subroutine waits for the user to enter the desired infusion rate (measured in units of milliliters per hour) and the desired total infusion volume (measured in milliliters). Once these two parameters have been entered and the user has pressed the Start key, the Set Up Subroutine of FIG. 5c calculates two values. First, the desired burettes per millisecond parameter is calculated by converting the desired infusion rate into the units of milliliters per millisecond and then by multiplying this quantity by a parameter having the units burettes per milliliter. In this preferred embodiment, the volumetric chamber 52 defines a volume between the upper and lower levels of 10 milliliters, and thus this parameter has the value 0.10. The program then calculates an initial drop rate (drops per millisecond). The initial drop rate is calculated as the product of a stored parameter (the assumed drops per burette) and the previously calculated parameter desired burettes per millisecond. Once these two quantities have been calculated and stored, the Set Up Subroutine of FIG. 5c returns control to the Main Control Sequence of FIG. 5a.

Figure 5D:
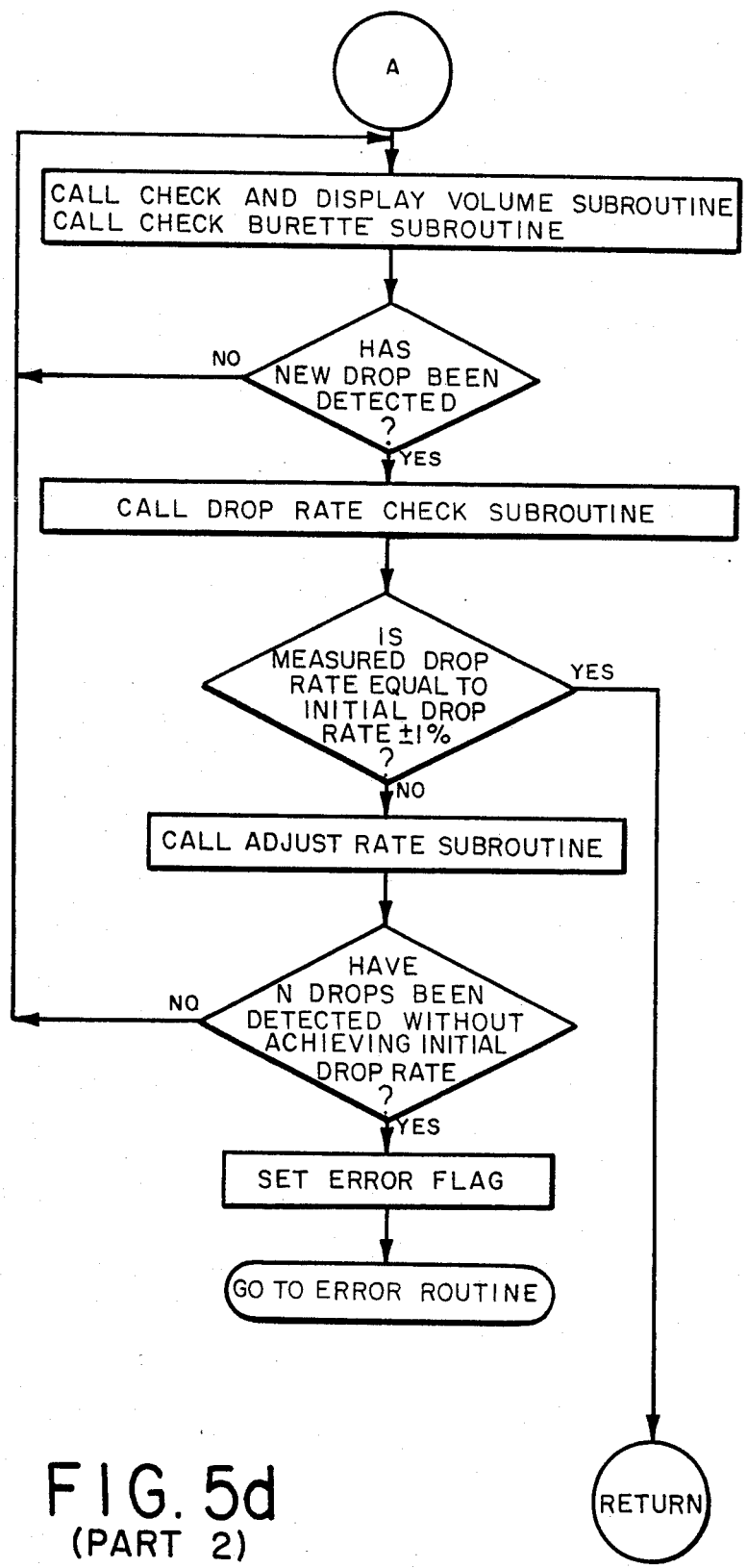

Next, the Start Flow Subroutine of FIG. 5d is executed. Generally speaking, this subroutine operates to control the motor 84 to adjust the position of the motor positioned pinch clamp jaw 86 such that the actual, measured drop rate (which is sensed by means of the light source 88 in the photosensor 90) is set equal to the just calculated initial drop rate. Once this condition is obtained, the motor 84 stopped and control is returned to the Main Control Sequence of FIG. 5a. In the event a predetermined number of drops fall before the actual drop rate is made to equal the initial drop rate, the subroutine of FIG. 5d sets an error flag and then calls an error routine flow charted in FIG. 5i. Thus, the Start Flow Subroutine of FIG. 5d sets the drop rate at a value which is determined as a function of stored parameters to produce approximately the desired infusion flow rate.

The Main Control Sequence of FIG. 5a then checks to determine if the desired volume has been infused or if the Stop key has been pressed by the user. If either of these conditions is found to obtain, the motor 84 is moved to a predetermined position (the Keep Vein Open or KVO position) to reduce the flow rate of fluid through the drip chamber 54 to a very low rate, sufficient to prevent the IV set 40 from clogging. The program then waits for intervention by the user.

Assuming the Stop key has not been pressed, the desired volume has not been infused, and no errors have been detected, the program then enters a flow rate adjustment mode which operates to adjust the drip rate repeatedly in order repeatedly to improve the accuracy with which the actual rate of fluid flow through the IV set 40 approximate the desired infusion rate. This loop includes a number of separate subroutines, as shown in FIGS. 5e through 5j.

Figure 5E:
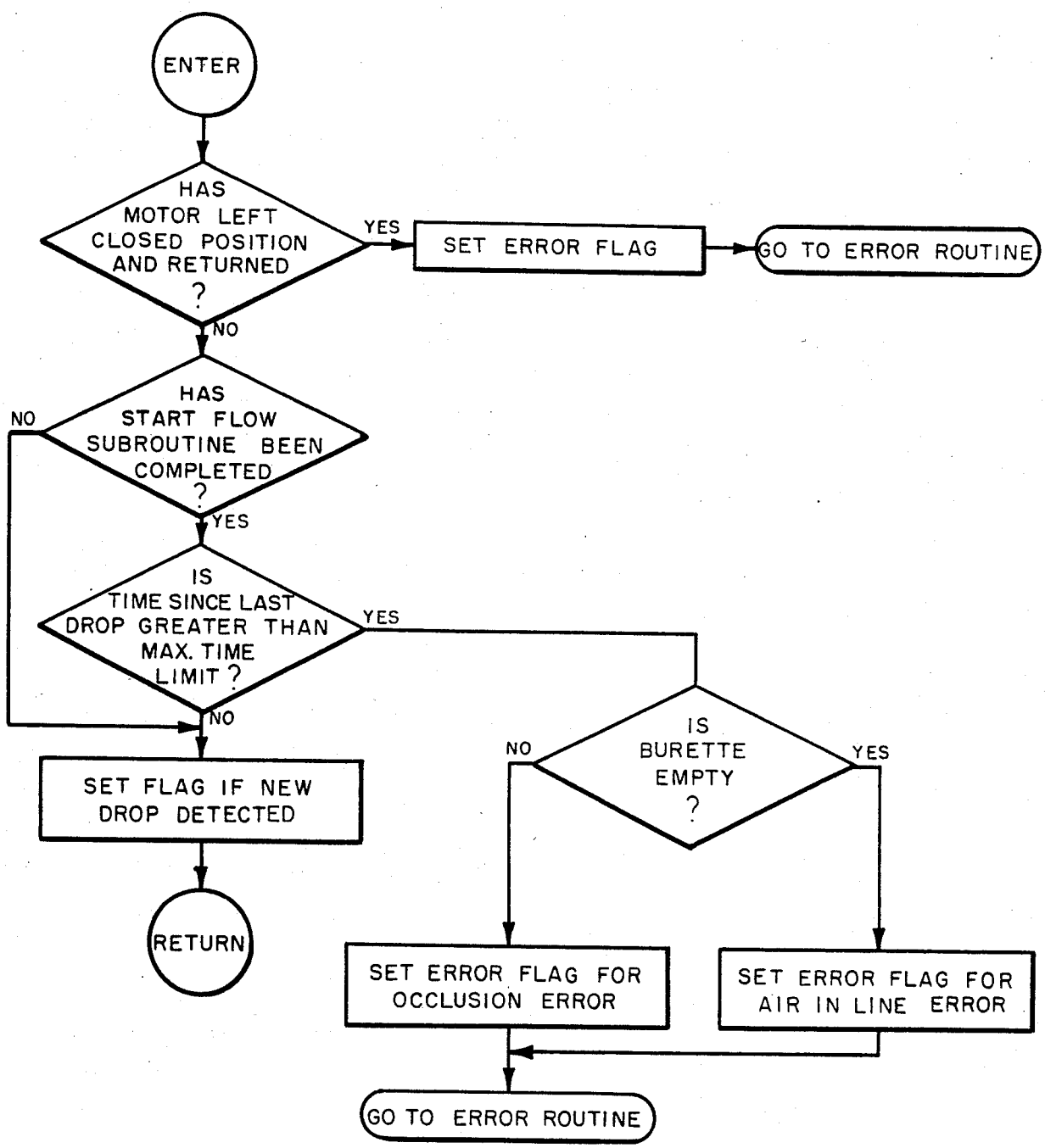
Figure 5F:
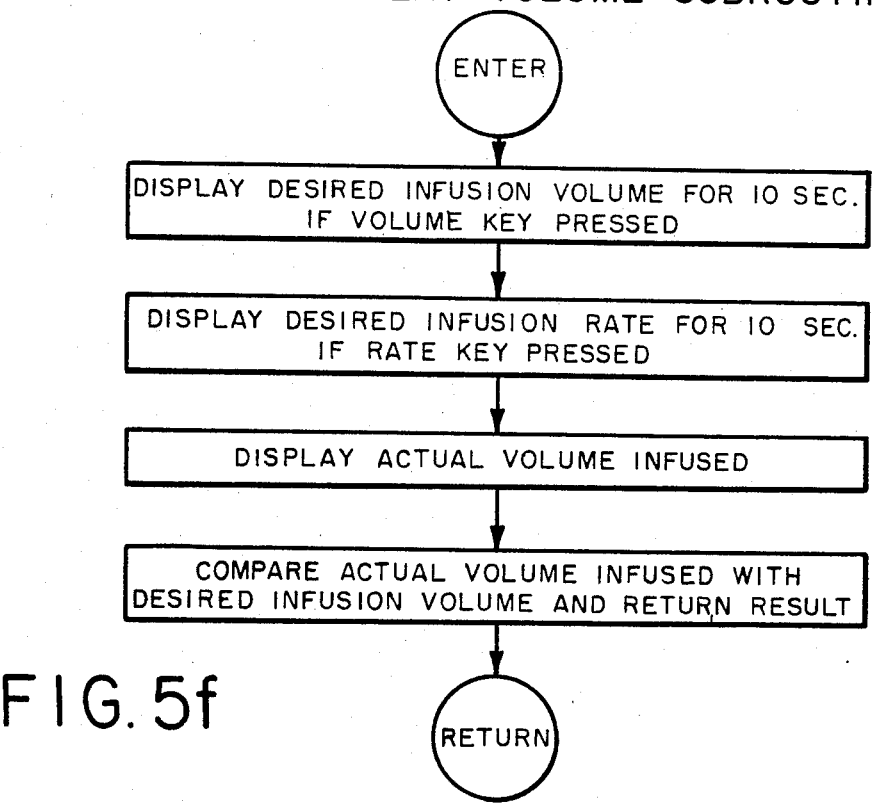

The Check and Display Volume Subroutine of FIG. 5f operates to control the display 14 in accordance with user requests. If the Volume key is pressed, the desired infusion volume is displayed for 10 seconds. If the Rate key is pressed, the desired infusion rate is displayed for 10 seconds. Otherwise, the actual volume infused is displayed. The subroutine also acts to compare the actual volume infused with the desired infusion volume and to return this result.

Figure 5G:
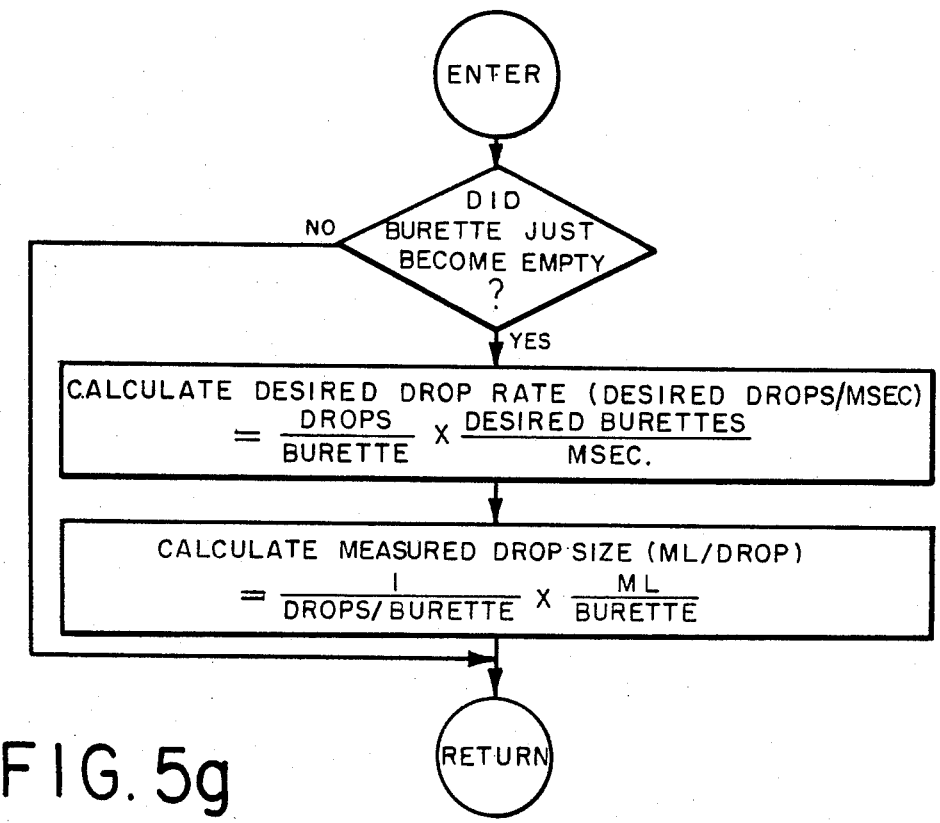

The subroutine of FIG. 5g is the Check Burette Subroutine. This subroutine first checks to determine if the burette just became empty, as indicated by the signal generated by the lower level photosensor 94. The routine simply returns without taking any action if the burette has not just become empty. However, if the burette has just become empty, the routine calculates the desired drop rate, a variable having the units of desired drops per millisecond. The desired drop rate is calculated as the product of the measured number of drops in the last burette times the desired burettes per millisecond. By counting the number of drops in each burette, the program in effect measures the actual volume of average drops of the burette and then uses this measured volume to adjust the desired drop rate. The first burette is infused using a stored estimate of the number of drops per burette. However, all subsequent burettes are infused at a drop rate which is determined as a function of the actual number of drops counted in the most recently infused burette. In this way, corrections are quickly made for variations in drop size due to changes in viscosity, pressure, or infusion rate. The Check Burette Subroutine of FIG. 5g also calculates the measured drop size by obtaining the product of the inverse of the total number of drops per burette multiplied by the known number of milliliters per burette.

FIG. 5e flowcharts the New Drop Subroutine. This subroutine first checks to determine whether the motor 84 has left the closed position and returned. If so, an appropriate error flag is set and the error routine is called. Otherwise, the program operates to check the time since the last drop against a maximum time limit. If the measured time is greater than the maximum time limit (indicating an excessively slow drop rate) the subroutine then determines whether or not the burette is emptly (as indicated by the lower level photosensor 94). If the burette is empty, the program sets an error flag to indicate air in the line and calls the error routine. If the burette is not empty, indicating no lack of fluid supply to the burette, the New Drop Subroutine then sets the error flag to indicate an occlusion error and calls the error routine. In the event that the time since the last drop is not greater than the maximum time limit, the routine sets a flag if a new drop has been detected and then returns.

Figure 5H:
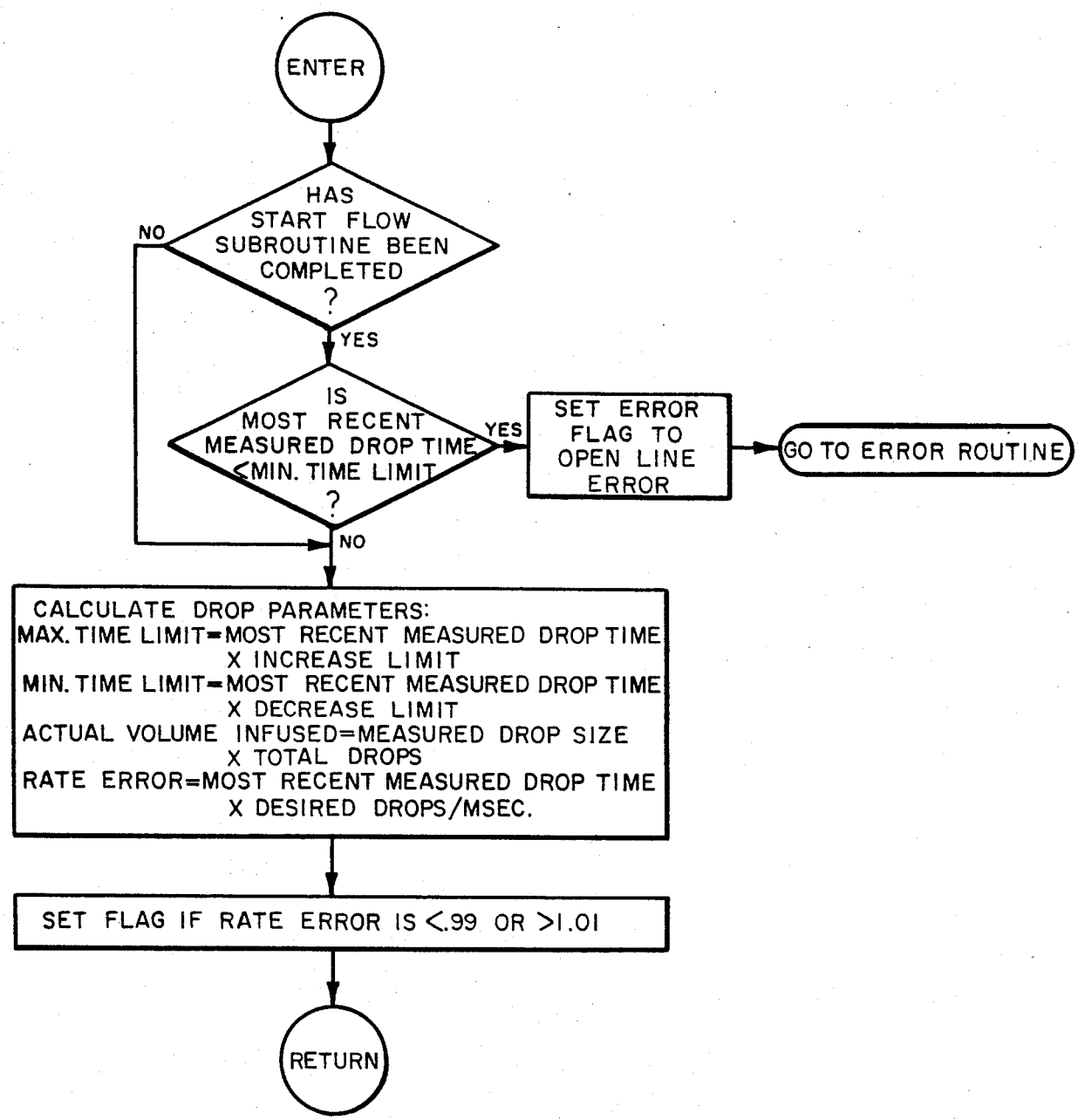

After each drop is detected, the Drop Rate Check Subroutine of FIG. 5h is executed. This subroutine first checks to determine if the most recently measured drop time is less than a minimum drop time limit. If so, the error flag is set to indicate an open line error, and the error routine is called. Otherwise, the subroutine calculates a number of parameters. First, it sets the maximum time limit equal to the most recently measured drop time times an increase limit (1.30 in this embodiment). The minimum time limit is then set equal to the most recently measured drop time times a decrease limit (0.80 in this embodiment). In this way, both the maximum and minimum time limits are allowed to track the actually measured drop time, as long as the actually measured drop time does not vary too abruptly. If it does, this abrupt change in the measured drop time is used as explained above as an indication of either an open line, an occlusion, or air in the line. This subroutine also calculates the actual volume infused, which is equal to the measured drop size as determined in the Check Burette Subroutine multiplied by the total number of drops infused. Finally, the Drop Check Subroutine calculates the rate error which is equal to the most recently measured drop time multiplied by the desired drops per millisecond as determined in the Check Burette Subroutine. The rate error is equal to 1 in the event the most recently measured drop time corresponds to an instantaneous drop rate equal to the desired drop rate. The subroutine of FIG. 5a sets a flag if the rate error is less than 0.99 (indicating that the instantaneously prevailing drop rate is less than the desired drop rate) or if the rate error is greater than 1.01 (indicating that the instantaneously prevailing drop rate is greater than the desired drop rate). The Drop Rate Check Subroutine then returns.

Figure 5I:
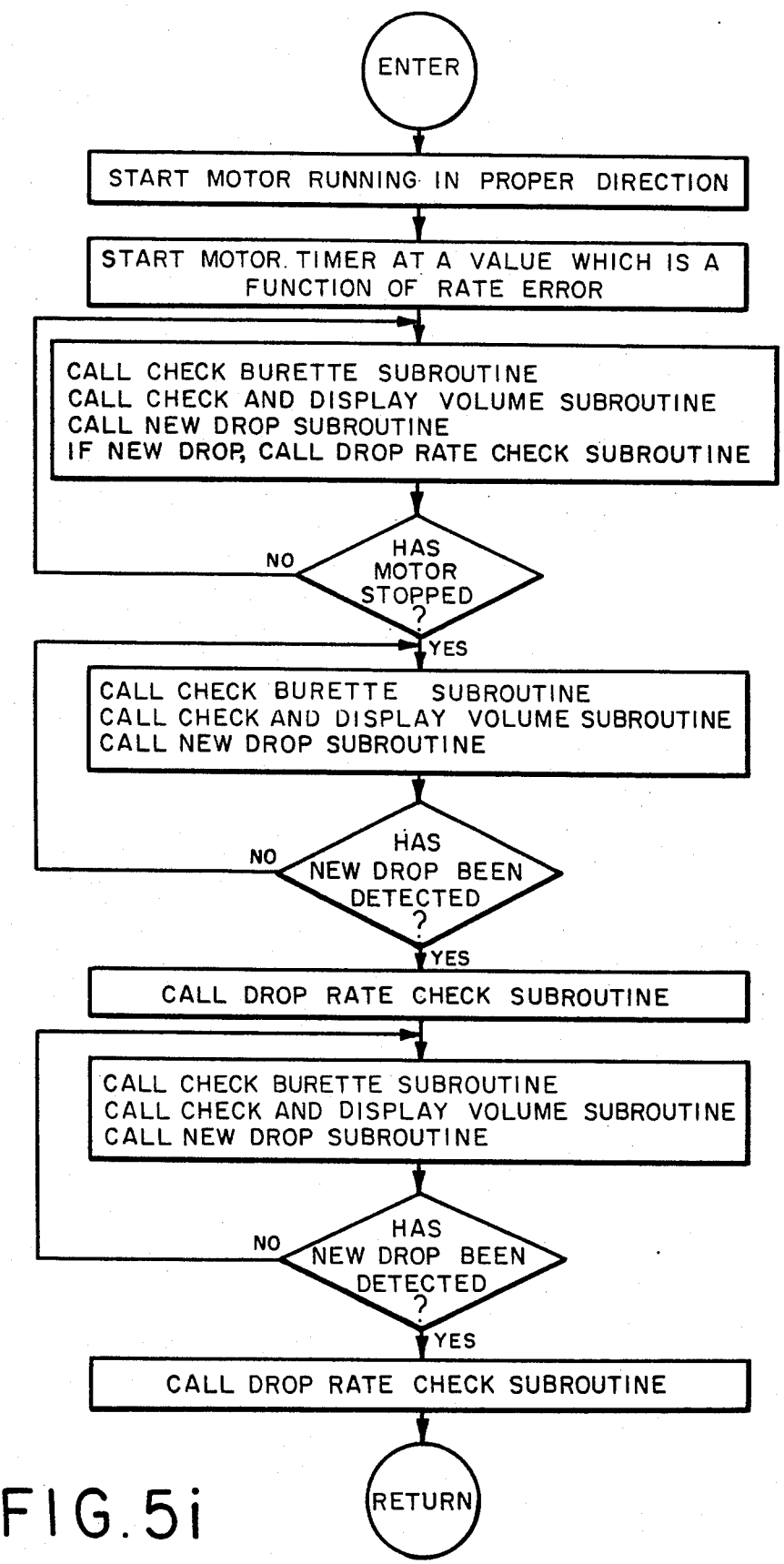

If the rate error is less than 0.99 or greater than 1.01, the Adjust Rate Subroutine of FIG. 5i is then executed. This subroutine starts the motor 84 running in the appropriate direction to bring the actual drop rate equal to the desired drop rate and then sets the motor timer at a value which is a function of the magnitude of the rate error. In general, larger rate errors result in larger initial values for the motor timer. The subroutine waits for the motor to stop, and then waits for two additional drops to be detected in order to allow the system to stabilize. The subroutine then returns.

Figure 5J:
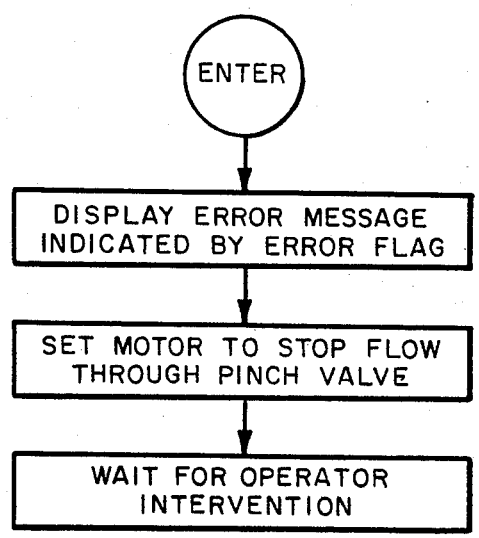

The Error Subroutine shown in FIG. 5j is a simple routine which merely displays the error message indicated by the error flag, sets the motor to stop all flow through the pinch valve, and then waits for intervention by the user.

Figure 5K:
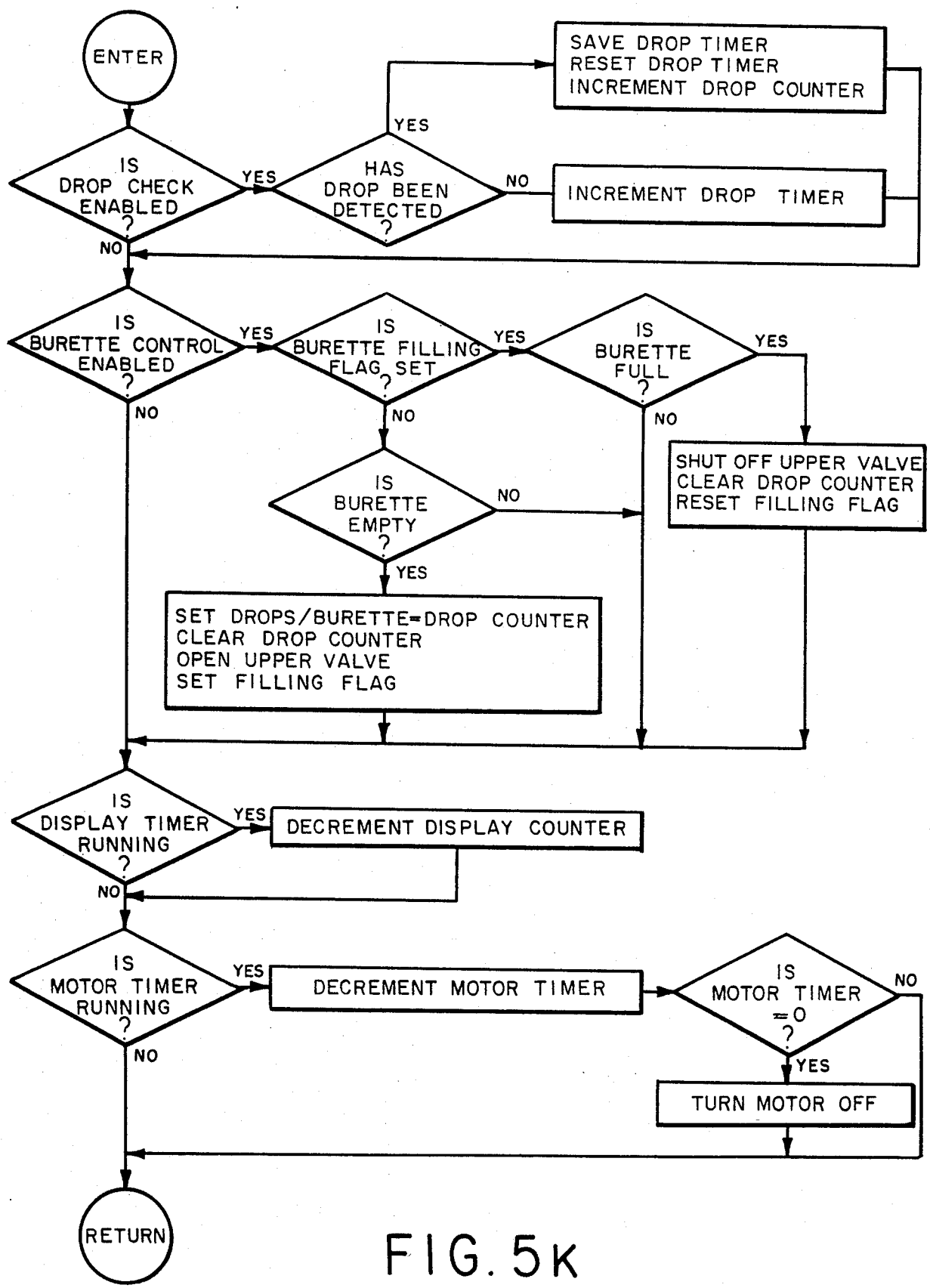

FIG. 5k shows the Interrupt Service Subroutine. This subroutine is executed periodically, at one millisecond intervals. The Interrupt Service Subroutine performs several functions. First, if the drop check function is enabled, the program monitors the output of the drop detector photosensor 90 to determine if a drop has been detected. If so, a drop timer is saved and then reset, and a drop counter is incremented. If no drop has been detected the drop timer is incremented. In this way, this subroutine acts both to time the period between adjacent drops and to count the total number of drops detected.

The routine of FIG. 5k also provides the burette control function described above. When the burette control function is enabled, the routine of FIG. 5k operates automatically to control the electromagnet 80 to energize the electromagnet 80 when the burette is empty and to deenergize electromagnet 80 when the burette is full. Furthermore, the routine controls relevant drop counters.

When the display timer is running the routine of FIG. 5k decrements the display counter with every pass through the routine. Similarly, when the motor timer is running the routine of FIG. 5k decrements the motor timer and checks to determine if the motor timer is equal to zero. If so, the routine of FIG. 5k turns the motor 84 off, and then returns.

OPERATION

In one mode of operation of the IV set 40 of this invention, the user snaps an IV set 40 in place in the controller 10 and then presses the Purge key. The controller 10 operates alternately to energize and deenergize the electromagnet 80 to maintain the fluid level in the volumetric chamber 52 between the lower fluid level and the upper fluid level sensors. During this time, fluid is free to drip through the drip chamber 54 to purge the IV set 40. Once the purge has been completed, the user then moves the pinch clamp lever 18 into the closed position. The controller 10 then stops all flow through the pinch valve and operates to fill the volumetric chamber 52 to the upper fluid level. At this point, the cannula or needle can be inserted into the patient and the system is ready to begin operation.

The user then keys in the desired infusion rate and the desired total volume to be infused and presses the Run button. The controller 10 then controls the motor 84 to release the lower pinch clamp to establish an initial drop rate which is determined as a function of a stored assume volume of each drop.

The electromagnet remains deenergized as the fluid level in the volumetric chamber 52 falls from the upper level to the lower level. During this time, the controller 10 operates automatically to monitor the drop detector photosensor 90 to control the motor 84 to maintain the initial drop rate. Furthermore, the total number of drops detected as the fluid level in the volumetric chamber 52 falls from the upper fluid level to the lower fluid level is counted. The controller then energizes the electromagnet 80 to refill the volumetric chamber 52 to the upper level.

The volume of the volumetric chamber 52 between the upper and lower level is a known quantity, and thus the average volume of each drop can be determined because the total number of drops required to infuse a known volume has been counted. This information is then used to revise the desired drop rate to take into account the currently prevailing volume of individual drops. The motor 84 is then automatically adjusted until the actual flow rate through the housing 48 is very closely equal to the desired flow rate initially entered by the user.

Each time the volumetric chamber 52 empties down to the lower level, the electromagnet 80 is energized to refill the chamber 52. Each time the volumetric chamber 52 empties, the flow rate for the most recently infused ten milliliters is compared to the desired rate set initially, and any slight corrections in the drop rate are made by means of the motor 84. Thus, after the first few tens of milliliters have been infused, the system provides extremely accurate control of the fluid flow rate. In alternate embodiments the controller can operate to measure the time required for the volumetric chamber to empty rather than to count the drops in the chamber in order to determine the actual infusion rate.

When the desired infusion volume has been reached, the controller will go into the KVO mode which is indicated on the display 14. The motor driven pinch clamps slows the drip rate to the KVO rate.

The controller 10 operates to indicate a number of separate errors distinctly and separately. For example, if the container 42 becomes empty during the infusion, the drop rate will fall below the minimum drop rate and the lower level photosensor will indicate that the volumetric chamber 52 is empty. When this condition is detected, the motor is automatically positioned to close off the tube 56 completely to prevent any air from passing to the patient. An audio alarm is sounded and an indicator is lighted on the display 14 indicating that an air in line error has been detected.

In the event of an occlusion such as a kink in the lower tube 56, the drop rate will slow below the minimum drop rate and the lower level photosensor 94 will indicate that the volumetric chamber 52 is not empty. Under these conditions, an audio alarm will be sounded and an indicator will be lighted on the display 14 identifying that an occlusion error has been detected.

In the event that an open line condition occurs (as for example if the needle or cannula pulls out of the patient), the sudden reduction in back pressure will cause the measure drop rate to increase abruptly above the maximum drop rate. This increase in the drop rate is sensed by the controller 10 to activate both an audio alarm and an indication on the display 14 that an open line error has been sensed. Once again, the motor 84 will be driven to cause the clamp to stop all flow through the IV set 40, and thereby to reduce the volume of fluid lost through the open line.

From the foregoing, it should be apparent that an intravenous set has been described which is compact and relatively inexpensive to manufacture. This intravenous set can be used as described above to provide the advantages of extremely accurately controlled infusion rates. In this way, the inaccuracies of conventional manually controlled IV sets are avoided, as are the cost, weight, and potential overpressure disadvantages of infusion pumps.

Of course, it should be understood that various changes and modifications to the preferred embodiments described above will be apparent to those skilled in the art. As described above, a wide range of valves and means for interrupting fluid flow into the volumetric chamber can be used, and the geometry of the volumetric chamber and the drip chamber can vary widely as well. Depending on the precise geometry chosen, it may be preferable to form the conduit 70 integrally with one of the walls of the volumetric chamber, or even to position the conduit 70 outside the volumetric chamber. Furthermore, the intravenous set of this invention can be adapted for use with controllers which utilize capacitive or conductive techniques to sense the fluid level inside the volumetric chamber or to detect drops formed in the drip chamber. Materials, dimensions and parameters such as the volume of the volumetric chamber can vary widely depending on individual applications. In many cases, it will be preferable to form the drop forming device which separates the volumetric chamber from the drip chamber of molded plastic materials, as described above.

It is therefore intended that the foregoing detailed description be regarded as illustrative rather than limiting, and that it be understood that it is the following claims, including all equivalents, which are intended to define the scope of this invention.

We claim:

1. In an intravenous set comprising an input port, first means for connecting the input port to a container, a tube, and second means for connecting the tube to an insertion device adapted to introduce fluids into a living subject, the improvement comprising:
   a drip chamber comprising means for forming fluid into drops, said drip chamber comprising means at a first location for accomodating remote detection of the rate at which drops are formed by the forming means;
   a volumetric chamber mounted upstream of the drip chamber such that fluids passing from the volumetric chamber flow to the drip chamber, a portion of said volumetric chamber having a precalibrated volume between a second and a third location spaced along the volumetric chamber and both separated from the first location, said portion comprising means for accomodating remote detection of the fluid level inside the volumetric chamber at said second and third locations of said volumetric chamber to indicate when said precalibrated volume has been emptied from the volumetric chamber;
   means for connecting the drip chamber to the tube such that the tube receives fluid which has flowed from the drip chamber; and
   means for connecting the volumetric chamber to the input port such that the volumetric chamber receives fluid which has flowed from the input port, said means for connecting the volumetric chamber to the input port comprising externally actuated means for selectively and reversably interrupting fluid flow from the input port to the volumetric chamber.

2. The invention of claim 1 wherein the interrupting means comprises:
   a valve seat; and
   a magnetically movable valve member configured to fit against the valve seat to block fluid flow therethrough in the absence of magnetic forces on the valve member.

3. The invention of claim 2 wherein the interrupting means further comprises:
   means for selectively retaining the valve member spaced away from the valve seat in the absence of magnetic forces on the valve member in order selectively to disable the interrupting means to allow fluids to flow freely through the valve seat.

4. The invention of claim 3 wherein the valve member comprises a ball and the retaining means comprises a pocket sized to receive and retain the ball.

5. The invention of claim 1 wherein the interrupting means comprises an externally actuated diaphragm valve.

6. The invention of claim 1 wherein the interrupting means comprises a collapsible conduit.

7. The invention of claim 1 wherein the means for accommodating remote detection of the fluid level inside the volumetric chamber comprises first and second optical windows situated at the upper and lower extremes, respectively, of the portion of the volumetric chamber, and wherein the volumetric chamber further comprises:
   a fluid inlet;
   a fluid outlet; and
   a conduit extending from the fluid inlet downstream of the second optical window to confine fluids passing into the volumetric chamber past the optical windows.

8. In an intravenous set comprising an input port, first means for connecting the input port to a container, a tube, and a second means for connecting the tube to an insertion device adapted to introduce fluids into a living subject, the improvement comprising:
- an enclosed housing coupled between the input port and the tube, said housing comprising upper and lower barrier means for segmenting the housing to define an upper valve chamber, a middle volumetric chamber, and a lower drip chamber;
- a magnetically responsive valve member positioned in the upper valve chamber;
- a valve seat included in the upper barrier means to interconnect the valve chamber and the volumetric chamber, said valve seat configured such that the valve member interrupts fluid flow from the valve chamber to the volumetric chamber in the absence of magnetic forces;
- means for accommodating remote detection of the fluid level inside the volumetric chamber at an upper and a lower location, said means for accommodating comprising upper and lower optically transmissive portions of the housing at upper and lower levels of the volumetric chamber, respectively, said upper and lower locations positioned such that the volume of that portion of the volumetric chamber bounded by the upper and lower levels is equal to a predetermined volume;
- a port included in the lower barrier means to interconnect the volumetric chamber and the drip chamber, said port terminating at its lower end in means for forming fluid passing therethrough into drops; and
- drip chamber means for accommodating remote detection of drops formed by a drop forming means, said drip chamber means comprising an additional optically transmissive portion of the housing beneath the drop forming means.

9. The invention of claim 8 wherein the magnetically movable member comprises a ball.

10. The invention of claim 8 wherein the magnetically movable member comprises a tiltable element having a longitudinal axis.

11. The invention of claim 8 wherein the invention further comprises:
- means for selectively retaining the valve member spaced from the valve seat in the absence of magnetic forces on the valve member to allow uninterrupted fluid flow from the valve chamber to the volumetric chamber.

12. The invention of claim 11 wherein the valve member comprises a ball and the retaining means comprises a pocket defined in a surface of the valve chamber and sized to receive and retain the ball.

13. The invention of claim 8 further comprising:
- a conduit extending from the valve seat to a point in the volumetric chamber beneath the lower location to confine fluid entering the volumetric chamber to a selected portion of the volumetric chamber.

14. In an intravenous set comprising an input port, first means for connecting the input port to a container, a tube, and second means for connecting the tube to an insertion device adapted to introduce fluids into a living subject, the improvement comprising:
- an enclosed housing coupled between the input port and the tube, said housing comprising barrier means for segmenting the housing to define a middle volumetric chamber and a lower drop chamber;
- means for defining an upper valve chamber upstream of the volumetric chamber;
- a valve member positioned in the upper valve chamber;
- a valve seat configured to cooperate with the valve member to form means for interrupting fluid flow from the valve chamber to the volumetric chamber when the valve member is in a sealing position;
- first means, included in the housing, for accommodating remote sensing of the fluid level in the volumetric chamber at at least two levels;
- a port included in the barrier means to interconnect the volumetric chamber and the drip chamber, said port terminating at its lower end in means for forming fluid passing therethrough into drops; and
- second means, included in the housing, for accommodating remote detection of drops formed by the drop forming means.

15. The invention of claim 14 wherein the valve member comprises a magnetically responsive element.

16. The invention of claim 15 wherein the magnetically responsive element comprises a ball.

17. The invention of claim 15 wherein the magnetically responsive element comprises a tiltable element having a longitudinal axis.

18. The invention of claim 15 wherein the invention further comprises:
- means for selectively retaining the valve member spaced from the valve seat in the absence of magnetic forces on the valve member to allow uninterrupted fluid flow from the valve chamber to the volumetric chamber.

19. The invention of claim 18 wherein the valve member comprises a ball and the retaining means comprises a pocket defined in a surface of the valve chamber and sized to receive and retain the ball.

20. The invention of claim 14 further comprising:
- a conduit extending from the valve seat to a point in the volumetric chamber beneath a lower one of the at least two levels to confine fluid entering the volumetric chamber to a selected portion of the volumetric chamber.

21. The invention of claim 14 wherein the first and second means comprise respective optical windows.

22. The invention of claim 14 wherein the upper valve chamber comprises a collapsable conduit, and wherein the valve member and the valve seat comprise opposed inner surfaces of the collapsable conduit.

23. In an intravenous set comprising an input port, first means for connecting the input port to a container, a tube, and a second means for connecting the tube to an insertion device adapted to introduce fluids into a living subject, the improvement comprising:
- an enclosed unitary housing coupled between the input port and the tube, said housing comprising a barrier which segments the housing into an upper volumetric chamber and a lower drip chamber adjacent to and below the upper volumetric chamber;
- a valve chamber defined by the connecting means upstream of the volumetric chamber, said valve chamber comprising a collapsible conduit which interrupts fluid flow from the connecting means to the volumetric chamber when pinched closed;
- means for accommodating remote detection of the fluid level inside the volumetric chamber at an upper and a lower location, said means for accommodating comprising upper and lower optically transmissive portions of the housing at upper and lower levels of the volumetric chamber, respectively, said upper and lower locations positioned such that the volume of that portion of the volumetric chamber bounded by the upper and lower levels is equal to a predetermined volume;

a port included in the barrier means and positioned to interconnect the volumetric chamber and the drip chamber, said port terminating at its lower end in means for forming fluid passing therethrough into drops; and drip chamber means for accommodating remote detection of drops formed by the drop forming means, said drip chamber means comprising an additional optically transmissive portion of the housing beneath the drop forming means.

* * * * *